US00PP11448P

United States Patent [19]

Bullis, III et al.

[11] Patent Number: Plant 11,448

[45] Date of Patent: Jul. 18, 2000

[54] NEOREGELIA PLANT NAMED 'DONGER'

[76] Inventors: Harvey R. Bullis, III; Patricia Gomez Bullis, both of 12420 SW. 248th St., Princeton, Fla. 33032

[21] Appl. No.: 09/135,398

[22] Filed: Aug. 18, 1998

[51] Int. Cl.[7] ..... A01H 5/00

[52] U.S. Cl. ..... Plt./370

[58] Field of Search ..... Plt./370

*Primary Examiner*—Howard J. Locker
*Assistant Examiner*—Michelle Kizilkaya
*Attorney, Agent, or Firm*—Foley & Lardner

[57] ABSTRACT

A new cultivar of Neoregelia named 'Donger', characterized by its leaves which are marginally striated with white markings which become bright pink when the plant is grown in bright light, its leaf centers which are medium green flushed with pink, and its miniature growth, highly branched, pendant habit which makes the new cultivar suitable for hanging baskets.

2 Drawing Sheets

BACKGROUND OF THE INVENTION

The present invention relates to a new and distinct cultivar of Neoregelia, a genus within the family bromeliaceae, referred to by the cultivar name 'Donger'. The new cultivar originated as a naturally occurring mutation of unknown causation from the unpatented cultivar 'Fireball'. The new cultivar was discovered by the inventors in a shadehouse in Princeton, Fla. The new cultivar was discovered as a whole plant growing among selected plants of the parent cultivar, and was recognized due to its colorful marginally variegated leaves.

Horticultural evaluation and selection of subsequent generations of propagation by off-shoots carried out by or under the direction of the inventors at Princeton, Fla., beginning in July 1990 has clearly demonstrated that the combination of characteristics as herein disclosed for the new cultivar 'Donger' are firmly fixed and are retained through successive generations of asexual reproduction.

'Donger' is primarily distinguished from the parent cultivar 'Fireball' and from other known Neoregelia cultivars by its leaves which are marginally variegated with white, which becomes pink with age and bright pink when the plants are grown in bright light.

Both 'Donger' and its parent are characterized by their pendant, highly branched, miniature habits suitable for hanging baskets. However, the foliage of 'Donger' is slightly lighter green in the leaf centers, and, as noted, is marginally striated with white to pink stripes. The leaf margins of 'Fireball' are green. 'Donger' has not been tested under all available environmental conditions. The phenotype may vary with variations in environmental conditions such as temperature, light intensity, day length and humidity without, however, any variance in genotype.

BRIEF DESCRIPTION OF THE DRAWING

The color photographic sheets show typical characteristics of 'Donger', with colors being as true as possible with illustrations of this type.

Sheet 1 depicts a clump of plants of 'Donger' after 12 months growth finished in a 15 cm pot.

Sheet 2 is a comparison photograph with 'Donger' appearing on the bottom left and 'Fireball' on the top right of the photo (supported by a pot).

DETAILED BOTANICAL DESCRIPTION

The following description is based on plants grown in Princeton, Fla., under the supervision of the inventor in greenhouse conditions which are typical of the industry. Color references are made to The Royal Horticultural Society (R.H.S.) Colour Chart.

Plant:

*Form and growth habit.*—Basal rosettes of strap-like leaves arranged around a central axis. Plants produce short runners which terminate in one or two new crowns. Plantings quickly become multi-branched, and frequently pendant.

*Height.*—Approximately 8–12 cm.

*Diameter.*—Approximately 22–29 cm.

Foliage:

*Size of leaf.*—The basal leaves are approximately 10–15 cm long, and 2.7–2.9 cm wide.

*Shape of leaf.*—The leaf blade is ligulate, with a broadly rounded, apiculate apex. The leaf is slightly channeled. The margins are entire with tiny spines.

*Leaf sheath.*—Broadly elliptic, approximately 6 cm long, and approximately 4 cm wide.

*Surface texture.*—The leaf blade is moderately thick, coriaceous, with a shiny surface.

*Color pattern.*—The leaves are variegated, having a medium green center, and white to pink striated margins. The variegated markings are visible from both sides of the leaf. The leaf surfaces are flushed with pink. The leaf bases about the center of the plant are frequently bright pink. When the plant is grown in bright light, the whole variegation becomes bright pink.

*Color, upper surface of leaves.*—Leaf center, 147 A–B, becoming flushed with 59 C–D with age. Leaf margin, white 158 D, becoming flushed with 59 C with age, and becoming substantially bright pink, 59 B–C when plant is grown in bright light. The coloration of the leaf bases often intensifies to 59 B in mature plants.

*Color, underside of leaves.*—Leaf center, 147 B, becoming flushed with 59 D with age. Leaf margin, white 158 D, becoming flushed with 59 D with age.

*Average number of leaves.*—The plant produces approximately 12–14 leaves per crown.

*Roots.*—Roots are yellow-green changing to brown, wiry with fine laterals.

Inflorescence: The inflorescence is inconspicuous, sessile, submerged in the center of the plant, and not of commercial significance. The plants typically do not flower in cultivation unless chemically induced.

Flowers:

*Individual flowes.*—Calyx — Three sepals present approximately 20 mm long, 146 D, 145 D in color. Corolla — Tubular, three petals present, approximately 30–35 mm long, 3–5 mm wide. Tube, 155 D, petals violet 93 A, fading to black.

Floral organs:

*Ovary.*—Inferior, 5 mm long, 155 B in color.

*Anthers.*—Six in number. Approximately 4 mm long, 10 D in color.

Seed characteristics: Fertile. Attempts by inventor to reproduce cultivar from seeds were unsuccessful.

Disease resistance: Similar to parent.

It is claimed:

1. A new and distinct cultivar of Neoregelia plant named 'Donger', substantially as illustrated and described.

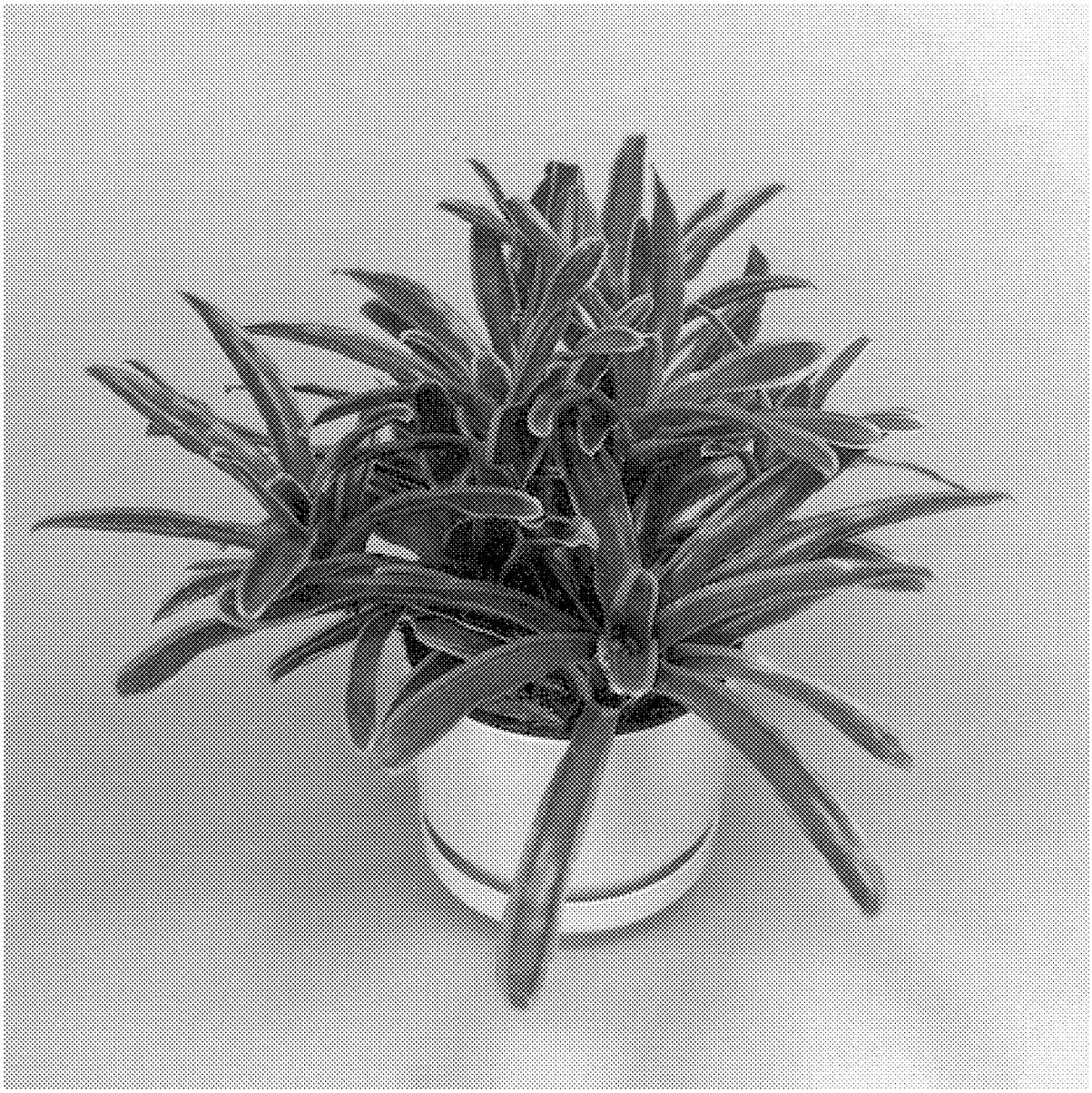

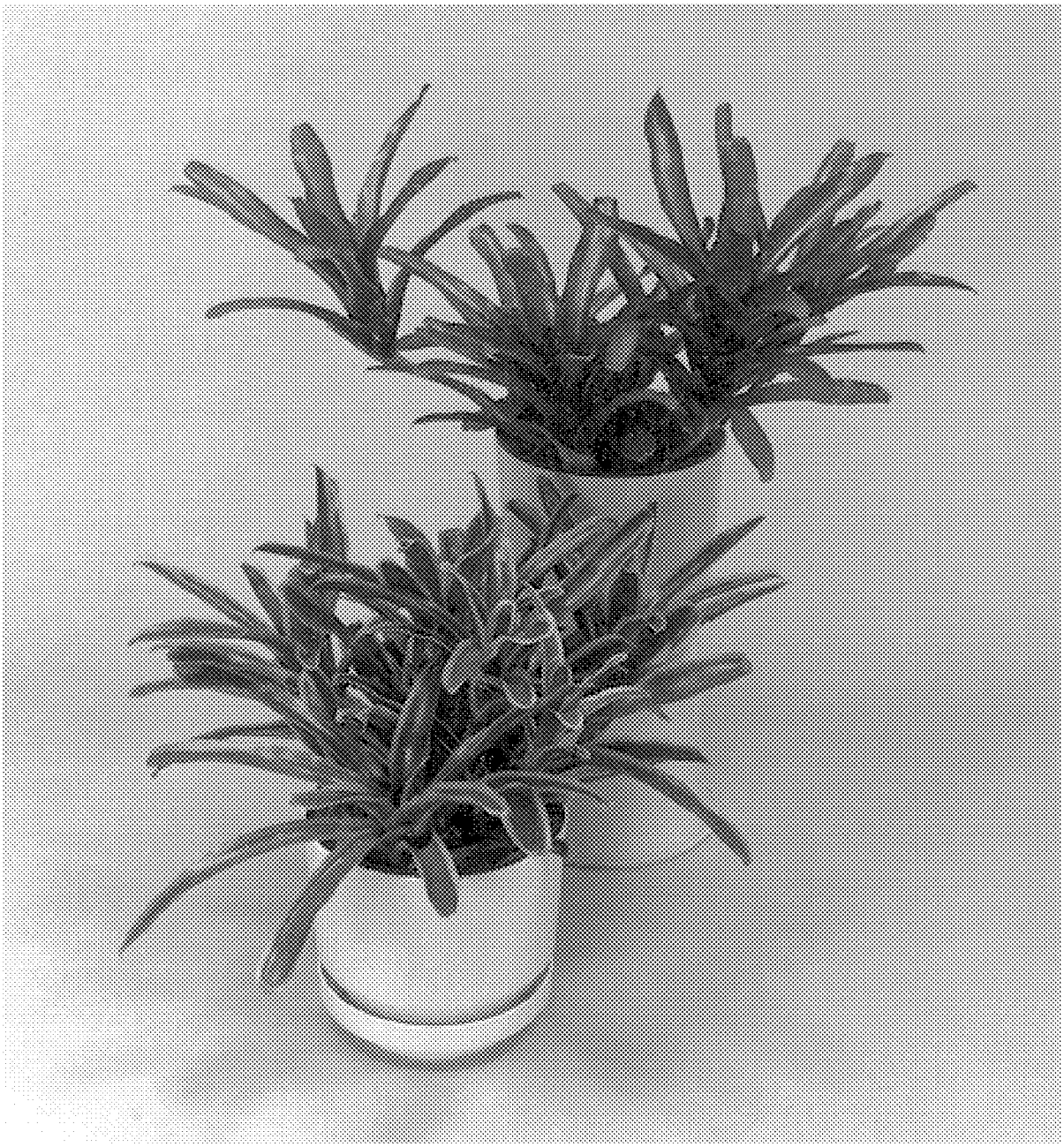

* * * * *